United States Patent
Jauchen et al.

(10) Patent No.: US 6,180,544 B1
(45) Date of Patent: Jan. 30, 2001

(54) AIR-PERMEABLE SUBSTRATE MATERIAL WITH A SELF-ADHESIVE COATING, PROCESS FOR ITS PRODUCTION AND ITS USE

(75) Inventors: Peter Jauchen, Hamburg; Peter Himmelsbach, Buxtehude, both of (DE)

(73) Assignee: Beiersdorf AG, Hamburg (DE)

( * ) Notice: Under 35 U.S.C. 154(b), the term of this patent shall be extended for 0 days.

(21) Appl. No.: 09/171,312

(22) PCT Filed: Apr. 26, 1997

(86) PCT No.: PCT/EP97/02177

§ 371 Date: Oct. 15, 1998

§ 102(e) Date: Oct. 15, 1998

(87) PCT Pub. No.: WO97/43992

PCT Pub. Date: Nov. 27, 1997

(30) Foreign Application Priority Data

May 18, 1996 (DE) .............................................. 196 20 109

(51) Int. Cl.⁷ ................... B32B 7/12; C09J 7/02
(52) U.S. Cl. ............. 442/150; 442/151; 428/317.3; 428/317.5; 428/317.7; 428/355 BL
(58) Field of Search ................... 442/150, 151; 428/317.1, 317.3, 317.5, 317.7, 343, 355 BL, 355 R

(56) References Cited

U.S. PATENT DOCUMENTS

| 4,163,822 | 8/1979 | Walter ................................. 428/304 |
| 4,762,888 | 8/1988 | Sun et al. ............................. 525/125 |
| 4,879,178 | 11/1989 | Sun et al. ............................ 428/355 |
| 5,194,455 | 3/1993 | Massow et al. ...................... 522/152 |
| 5,342,858 | 8/1994 | Litchholt et al. ...................... 521/98 |
| 5,605,717 * | 2/1997 | Simmons et al. ................. 427/208.2 |

FOREIGN PATENT DOCUMENTS

| 4237252 | 5/1994 | (DE) ................. C09J/7/02 |
| 4308649 | 9/1994 | (DE) ............. A61L/15/42 |
| 0353972 | 2/1990 | (EP) ............. A61F/13/02 |
| 0436159 | 7/1991 | (EP) ................. C09J/7/02 |
| 0578151 | 1/1994 | (EP) ............. C09J/133/08 |
| 2319699 | 2/1977 | (FR) ................. C09J/5/00 |
| 50-004993 | 2/1975 | (JP) ................. C09J/7/04 |
| 95/01408 | 1/1995 | (WO) ........... C09J/153/02 |

\* cited by examiner

*Primary Examiner*—Daniel Zirker
(74) *Attorney, Agent, or Firm*—Norris McLaughlin & Marcus P.A.

(57) ABSTRACT

Carrier material having a self-adhesive finish and a hotmelt self-adhesive composition applied to the entire area of at least one side, characterized in that the thermoplastic adhesive composition is foamed and the product has an air permeability of at least 3 $cm^3/cm^2/s$ for an amount applied of at least 20 $g/m^2$.

11 Claims, No Drawings

AIR-PERMEABLE SUBSTRATE MATERIAL WITH A SELF-ADHESIVE COATING, PROCESS FOR ITS PRODUCTION AND ITS USE

The invention relates to air-permeable carrier materials with a self-adhesive finish which are coated over the entire area of at least one side with a hotmelt self-adhesive composition, to a process for their preparation and to their use.

Hotmelt self-adhesive compositions based on natural and synthetic rubbers and on other synthetic polymers are known and are increasingly being employed. Their essential advantage is that, unlike the compositions which are applied from solution or as an aqueous dispersion, there is no need for the laborious and in some cases environmentally polluting methods of removing the solvents or the water.

It has already been proposed to employ self-adhesive compositions of this kind, especially those based on acrylates, for medical properties, in which case air-permeable woven fabrics or nonwovens are also mentioned as carrier material (U.S. Pat. No. 4,762,888, U.S. Pat. No. 4,879,178, EP-B 436 159 and EP-B 578 151). A disadvantage of these products coated over their entire area, however, is their inadequate permeability to air and water vapour. Moreover, an improvement in the adhesion properties can usually only be achieved by a higher amount of composition being applied.

In addition, it is known to apply such self-adhesive compositions not only over the entire area but also in a dot pattern, for example by screen printing (DE-C 42 37 252), in which case the dots of adhesive can also be distributed with varying sizes and/or varying distribution (EP-B 353 972), or by intaglio printing, in lines which join one another in the longitudinal and transverse direction (DE-C 43 08 649).

The advantage of the patterned application is that, given an appropriately porous carrier material, the adhesive materials are permeable to air and water vapour and in general are readily redetachable.

A disadvantage of these products, however, is that if the area covered by the adhesive film, which per se is impermeable, is too large there is a corresponding reduction in the permeability to air and water vapour, and the consumption of adhesive composition rises, and if the area covered by the adhesive film is too low the adhesion properties suffer, i.e. the product becomes detached too readily from the substrate.

In accordance with WO 95/01408, specific elasto-meric hotmelt adhesive foams based on block copolymer are employed as laminating adhesive in the production of nappies, although the only critical factor is their elastic properties.

The object of the invention, therefore, was to avoid the abovementioned disadvantages and to develop a product and process which features—given an appropriately porous carrier material—very good permeability to air and water vapour and also generally good adhesion properties coupled with low consumption of adhesive composition.

This object is achieved by an air-permeable carrier material having a self-adhesive finish and a hotmelt adhesive composition applied to the entire area of at least one side, which material is characterized in that the thermoplastic adhesive composition is foamed and the product has an air permeability of at least 3 $cm^3/cm^2/s$, preferably 30–160 $g/m^2$, for an amount applied of at least 20 $g/m^2$.

Products which have proved particularly suitable are those having an air permeability of 3–150 $cm^3/cm^2/s$, preferably 15–125 $cm^3/cm^2/s$ and, in particular, 25–100 $cm^3/cm^2/s$.

At the same time, the water-vapour permeability should be at least 100 $g/m^2/24$ h, preferably 100–5000 $g/m^2/24$ h and, in particular, 500–3000 $g/m^2/24$ h.

Depending on the carrier material and its sensitivity to temperature, the self-adhesive layer can be applied directly or first applied to an auxiliary carrier and then transferred to the ultimate carrier. Subsequent calendering of the coated product and/or pretreatment of the carrier, such as corona irradiation, for better anchorage of the adhesive layer, may also be advantageous.

The adhesive compositions are preferably foamed using inert gases such as nitrogen, carbon dioxide, noble gases, hydrocarbons or air, or mixtures thereof. In some cases, foaming by thermal decomposition of gas-evolving substances such as azo, carbonate and hydrazide compounds has also been found to be appropriate.

The degree of foaming, i.e. the proportion of gas, should be at least about 10% by volume and can range up to about 80%. In practice, values of 30–70%, preferably 50% proportion of gas have become well established. Operation at relatively high temperatures of about 100° C. and at a comparatively high internal pressure produces very open-pored adhesive foam layers which are of particularly good permeability to air and water vapour.

Self-adhesive compositions which can be employed are the known thermoplastic hotmelt adhesive compositions based on natural and synthetic rubbers and on other synthetic polymers such as acrylates, methacrylates, polyurethanes, polyolefins, polyvinyl derivatives, polyesters or silicones with appropriate additives such as adhesion resins, plasticizers, stabilizers and other auxiliaries where necessary. Their softening point should be higher than 80° C., since the application temperature is generally at least 90° C., preferably between 120 and 150° C. or 180–220° C. in the case of silicones. If desired, post-crosslinking by UV or electron-beam irradiation may be appropriate.

Self-adhesive compositions which have proven particularly suitable are those based on A-B-A block copolymers which consist of hard and soft segments. A is preferably a polymer block based on styrene and B is preferably a polymer block based on ethylene, propylene, butylene, butadiene, isoprene or mixtures thereof such as ethylene/butylene. In addition, such hotmelt adhesive compositions generally comprise one or more aliphatic or aromatic hydrocarbon resins as adhesion resins, one or more medium- or long-chain fatty acids or esters thereof and also stabilizers and, if desired, other auxiliaries. The ranges of amounts of constituents are usually between 15–70% block copolymers, 20–70% adhesion resins, 10–50% plasticizers and small amounts of stabilizers and other auxiliaries.

Carrier materials which can be employed are virtually all carriers which are air-permeable and porous per se and are customarily used for industrial or medical purposes, i.e. woven or knitted fabrics, elastic or inelastic materials, plastics films, papers, nonwovens, foam materials or laminates thereof.

The carrier materials having a self-adhesive finish which are coated in accordance with the invention with a foamed hotmelt self-adhesive composition are notable for a range of advantages. As a result of the foaming of the adhesive composition and the consequentially open pores in the composition, the products coated with the adhesive composition are of good permeability to water vapour and air when an inherently porous carrier is used. The amount of adhesive composition required is considerably reduced without adversely affecting the adhesion properties. The adhesive compositions have a surprisingly high tack, since per gram of composition more volume and thus adhesive surface area is available for the wetting of the substrate on which bonding is to take place, and the plasticity of the adhesive compositions is increased as a result of the foam structure. In addition, anchorage on the carrier material is thereby improved. Furthermore, the foamed adhesive coating gives the products a soft and smooth feel.

As a result of the foaming, moreover, the viscosity of the adhesive compositions is generally lowered. This saves on melting energy, and it is also possible to carry out direct coating of thermally unstable carrier materials.

The subjective product advantages of tack and smoothness can be quantified readily using a dynamo-mechanical frequency measurement. In this case, use is made of a rheometer controlled by shear stress.

The results of this measurement method give information on the physical properties of a material through taking into account the viscoelastic component. In this case, at a predetermined constant temperature, the pressure-sensitive hotmelt adhesive is set in oscillation between two plane-parallel plates with variable frequencies and low deformation (region of linear viscoelasticity). By way of a pickup control unit, with computer assistance, the quotient ($Q = \tan \delta$) between the loss modulus ($G''$, viscous component) and the storage modulus ($G'$, elastic component) is determined. A high frequency is chosen for the subjective sensing of the tack and a low frequency for the smoothness, and the corresponding quotients are determined from the degree of foaming. The higher the corresponding numerical value of the quotient, the better the subjective property.

It was possible in accordance with the invention to improve the tack and smoothness, as shown in the table.

| Designation | Smoothness low frequency/RT | Tack high frequency/RT |
|---|---|---|
| Pressure-sensitive hotmelt adhesive A (unfoamed) | $\tan \delta = 0.35 \pm 0.05$ | $\tan \delta = 0.45 \pm 0.05$ |
| Pressure-sensitive hotmelt adhesive A foam vol. ($N_2$) = 50% | $\tan \delta = 0.46 \pm 0.05$ | $\tan \delta = 0.65 \pm 0.05$ |
| Pressure-sensitive hotmelt adhesive A (unfoamed) | $\tan \delta = 0.35 \pm 0.05$ | $\tan \delta = 0.45\ 4 \pm 0.05$ |
| Pressure-sensitive hotmelt adhesive A foam vol. ($N_2$) = 70% | $\tan \delta = 0.58 \pm 0.05$ | $\tan \delta = 0.88 \pm 0.05$ |
| Pressure-sensitive hotmelt adhesive B (unfoamed) | $\tan \delta = 0.05 \pm 0.03$ | $\tan \delta = 0.84 \pm 0.05$ |
| Pressure-sensitive hotmelt adhesive B foam vol. ($N_2$) = 50% | $\tan \delta = 0.27 \pm 0.05$ | $\tan \delta = 1.15 \pm 0.05$ |
| Pressure-sensitive hotmelt adhesive C (unfoamed) | $\tan \delta = 0.06 \pm 0.03$ | $\tan \delta = 0.93 \pm 0.05$ |
| Pressure-sensitive hotmelt adhesive C foam vol. ($N_2$) = 50% | $\tan \delta = 0.31 \pm 0.05$ | $\tan \delta = 1.25 \pm 0.05$ |

Various pressure-sensitive hotmelt adhesives were chosen, i.e. A based on acrylate and B and C on block copolymers, and the results indicate a marked increase in the tan δ values as a result of foaming, i.e. a measurably better smoothness and tack.

The advantages demonstrated make the novel carrier materials particularly suitable for medical purposes. Plasters or bandages, or dressings additionally provided with a wound pad, for example, produced there-from are particularly good in their skin compatibility given an appropriately selected air-permeable carrier material and a hypoallergenic adhesive composition, since they are of pronounced permeability to air and water vapour over the entire surface and are soft and smooth. They have a cushioned effect and, as a result, couple good properties when being worn with good adhesion.

The product advantages as a result of the foaming of the adhesive compositions, such as high adhesive strength and good permeability to air and water vapour, can be derived from the following measurements.

1. Plaster bandages with foamed hotmelt adhesive compositions stick more strongly on the skin than plaster bandages with unfoamed adhesive compositions, with identical amounts of composition applied. Since the adhesive force on the skin varies from one skin type to another, the unfoamed adhesive composition was given an index of 100 and the foamed plaster bandage was related thereto. This gave the following results:

Index=adhesive force on the skin (foamed)/adhesive force on the skin (unfoamed)

TABLE 1

| | Increase in adhesive force on skin | | |
|---|---|---|---|
| Amount applied | Woven fabric (inelast.) | Woven fabric (elast.) | Nonwoven |
| 40 g/m² | 105–110% | | |
| 60 g/m² | | | 120–130% |
| 80 g/m² | 110–125% | 110–120% | |
| 120 g/m² | 120–170% | | |

2. Plaster bandages with foamed hotmelt adhesive compositions are more air-permeable than plaster bandages with unfoamed adhesive compositions, for the same amount of composition applied. The air permeability of plaster bandages with unfoamed adhesive compositions was <1 cm³/cm²/sec in the case of the samples tested. The air permeabilities relate to a degree of foaming of 50% in the end product.

TABLE 2

| | Air permeability as a function of amount applied | | | |
|---|---|---|---|---|
| Amount applied | Woven fabric (in-elast.) | Woven fabric (elast.) un-stretched | Woven fabric (elast.) stretched | Nonwoven |
| 40 g/m² | 6–19 cm³/cm²/sec | | | |
| 60 g/m² | | | | 90–100 cm³/cm²/sec |
| 80 g/m² | 3–8 cm³/cm²/sec | 20–35 cm³/cm²/sec | 90–110 cm³/cm²/sec | |
| 120 g/m² | 0–5–3 cm³/cm²/sec | | | |

3. The air permeability is dependent on the degree of foaming. The results were found for an amount applied of 80 g/m².

TABLE 3

Dependency of air permeability on the degree of foaming

| Degree of foaming | inelast. woven fabric |
|---|---|
| 30% | 2–5 cm$^3$/cm$^2$/sec |
| 50% | 3–8 cm$^3$/cm$^2$/sec |
| 70% | 7–25 cm$^3$/cm$^2$/sec |

4. In addition, the permeability for water vapour is particularly important for the skin. Similar plaster bandages with unfoamed adhesive compositions are not permeable to water vapour. The samples shown were conditioned beforehand at 23.5° C. Exemplary testing parameters are the temperature 37° C., the saturation vapour pressure 6.274 kPa and the relative atmospheric humidity 30%.

TABLE 4

Water vapour permeability rate as a function of amount applied

| Amount applied | Woven fabric (inelast.) in g/m$^2$/24 h | Woven fabric (elast.) unstretched in g/m$^2$/24 h | Nonwoven in g/m$^2$/24 h |
|---|---|---|---|
| 40 g/m$^2$ | 1020 | | |
| 60 g/m$^2$ | | | 2740 |
| 80 g/m$^2$ | 520 | 2510 | |
| 120 g/m$^2$ | 138 | | |

5. The dependency of water-vapour permeability on the degree of foaming is shown below. For this purpose, an amount applied of 80 g/m$^2$ was chosen. The parameters described in section 4 remained constant.

TABLE 5

Water-vapour permeability rate as a function of the degree of foaming

| Degree of foaming | inelast. woven fabric in g/m$^2$/24 h |
|---|---|
| 30% | 240 |
| 50% | 520 |
| 70% | 990 |

Cohesive adhesion coatings i.e. anti-slip coatings which stick only to themselves or have a virtually non-adhering character, can also be produced in accordance with the invention.

The advantageous properties of the novel adhesive coatings, such as low consumption of adhesive, high tack and good smoothness on both irregular and even surfaces, as a result of the elasticity and plasticity of the foamed adhesive compositions, can also be utilized in a purely industrial field. The resulting self-adhesive tapes and other products given a self-adhesive finish in this way are versatile in their possibilities for employment.

A particularly suitable process for producing the carrier materials given a self-adhesive finish in accordance with the invention operate in accordance with the foam-mix system. In this case, the thermoplastic pressure-sensitive adhesive is reacted under high pressure at about 120 degrees Celsius with dry gases, for example nitrogen, air or carbon dioxide in various proportions by volume (about 10–80%), in a stator/rotor system. While the gas feed pressure is >100 bar, the mixing pressures of gas/thermoplastic in the system are 40–100 bar, preferably 40–70 bar. The pressure-sensitive adhesive foam produced in this way passes via a line to the nozzle applicator system of a melt coating unit.

The invention is illustrated in more detail by means of examples.

EXAMPLE 1

For the functional tape dressings which are customary in orthopaedics, relatively rigid, inelastic woven fabrics are employed. Tape dressings are used for immobilizing the apparatus of motion and as support dressings for, inter alia, prophylaxis, first aid, therapy and restoration. For this purpose, rigid carrier materials with a maximum tensile force of about 60 N/cm and a maximum tensile-force elongation of less than 20% are coated on one side with an adhesive composition.

In accordance with the invention, a foamed hotmelt adhesive composition based on a block copolymer was used. To this end, rigid woven fabrics were coated with about 40, 80 and 120 g/m$^2$. All samples stick to the skin and are air-permeable. The greater the amount of adhesive composition applied, the stronger the bonding of the bandage to the skin. The air permeability decreases as the amount of composition applied goes up. The bandage finished with 40 g/M$^2$ of adhesive composition showed the best permeability to water vapour. The degree of foaming was about 50%.

It was thereby possible to show that the permeability to air and water vapour depend functionally on the amount of composition applied.

Furthermore, rigid woven fabrics were produced with different degrees of foaming. In this case, the functional relationship of the permeability to air and water vapour as a function of the degree of foaming is evident. The higher the proportion of gas in the applied adhesive composition, the greater the permeability. Products with a degree of foaming of 70% had the highest permeability in the experimental series (Tab. 3 and Tab. 5).

Samples with the same adhesive composition which, however, is unfoamed exhibit markedly lower permeabilities if any.

EXAMPLE 2

To date, elastic bandages have generally been coated indirectly. In this context, the adhesive composition is spread onto silicone-coated release paper and the solvent is removed in a drying tunnel. The elastic carrier material, a woven or knitted material, is then laminated on. However, a bandage produced in this way is not always of sufficient air-permeability.

A bandage produced in accordance with the invention was coated by the hotmelt coating process with a nitrogen-foamed adhesive composition based on a block copolymer, with an amount applied of about 80 g/m$^2$. The block copolymer is a styrene-ethylene-butylene-styrene block copolymer to which paraffinic hydrocarbons have been added. The ratio was one part of polymer to one part of paraffinic hydrocarbon. 10% of polystyrene resin (e.g. Amoco 18240) were added to the mixture produced. The adhesive also contained one per cent of anti-ageing agent (n-octadecyl β-(3,5-di-t-butyl-4-hydroxyphenyl)-propionate, trade name IRGANOX 1076) and further hydrocarbon resins and fatty acid esters, which are present only in small amounts in the overall adhesive. The adhesive is obtainable commercially (from Fuller). The adhesive composition was foamed with nitrogen in a ratio of 1:2 at 120°

C. by the method described above. The resulting proportion of gas in the end product was then 50%.

The air permeability of the bandage was 20–35 cm$^3$/cm$^2$/s in the unstretched state and about 100 cm$^3$/cm$^2$/s in the stretched state. The water-vapour permeability was greater than 500 g/m$^2$/24 h. As a result of the foamed, partially open-pored adhesive composition, the bandage is permeable to air and water vapour even in a multilayer dressing. It is employed for compression, support and release bandages, the high immediate and long-term adhesive force being advantageous. Furthermore, as a result of the elasticity of the adhesive, the adhesive composition based on the block copolymer supports the compressive action of the bandage. The modelling properties and user perception were improved by the foaming of the adhesive composition.

What is claimed is:

1. An air-permeable adhesive tape, plaster, bandage or dressing comprising an air-permeable carrier material having a thermoplastic hotmelt self-adhesive composition applied to the entire area of at least one side, wherein the thermoplastic adhesive composition is foamed and said adhesive tape, plaster, bandage or dressing has an air permeability of at least 3 cm$^3$/cm$^2$/s for an applied amount of adhesive composition of at least 20 g/m$^2$.

2. Air-permeable adhesive tape, plaster, bandage or dressing according to claim 1, having an air-permeability of 3–150 cm$^3$/cm$^2$/s.

3. Air-permeable adhesive tape, plaster, bandage or dressing according to claim 1, wherein the amount of adhesive composition applied is 30–200 g/m$^2$.

4. Air-permeable adhesive tape, plaster, bandage or dressing according to claim 1, having a water-vapor permeability of at least 100 g/m$^2$/24 hr.

5. Air-permeable adhesive tape, plaster, bandage or dressing according to claim 4, having a water-vapor permeability of 100–500 g/m$^2$/hr.

6. Air-permeable adhesive tape, plaster, bandage or dressing according to claim 1, wherein the adhesive composition is foamed using an inert gas selected from the group consisting of nitrogen, carbon dioxide, noble gases, hydrocarbons, air and mixtures thereof.

7. Air-permeable adhesive tape, plaster, bandage or dressing according to claim 1, wherein the proportion of gas in the adhesive composition is 10–80 per cent by volume.

8. Air-permeable adhesive tape, plaster, bandage or dressing according to claim 1, wherein the adhesive composition is composed on the basis of an A-B-A block copolymer, A being polystyrene and B being selected from the group consisting of ethylene, propylene, butylene, butadiene, isoprene and mixtures thereof.

9. Process for producing the air-permeable adhesive tape, plaster, bandage or dressing of claim 1, wherein the hotmelt adhesive composition is mixed under high pressure with inert gases in a proportion by volume of 10–80% in a stator/rotor system to produce a pressure-sensitive adhesive foam which is then passed into the supply nozzle of a melt coating devise, and is applied thereby to the carrier material.

10. Medical products comprising an air-permeable adhesive tape, plaster, bandage or dressing according to claim 1.

11. Medical products according to claim 10, wherein said medical products are selected from the group consisting of sticking plasters, fixing plasters, test plasters, rapid dressings, orthopaedic bandages, wound pads, incision films and colostomy bags.

* * * * *